(12) United States Patent
Quellec et al.

(10) Patent No.: US 10,083,507 B2
(45) Date of Patent: Sep. 25, 2018

(54) METHOD FOR THE ANALYSIS OF IMAGE DATA REPRESENTING A THREE-DIMENSIONAL VOLUME OF BIOLOGICAL TISSUE

(71) Applicant: MIMO AG, Bern (CH)

(72) Inventors: Gwenolé Quellec, Brest (FR); Jens Kowal, Seftigen (CH); Peter Maloca, Lucerne (CH)

(73) Assignee: MIMO AG, Bern (CH)

( * ) Notice: Subject to any disclaimer, the term of this patent is extended or adjusted under 35 U.S.C. 154(b) by 57 days.

(21) Appl. No.: 15/302,407

(22) PCT Filed: Mar. 30, 2015

(86) PCT No.: PCT/CH2015/000048
§ 371 (c)(1),
(2) Date: Oct. 6, 2016

(87) PCT Pub. No.: WO2015/154199
PCT Pub. Date: Oct. 15, 2015

(65) Prior Publication Data
US 2017/0032525 A1  Feb. 2, 2017

(30) Foreign Application Priority Data
Apr. 7, 2014  (CH) .......................... 534/14

(51) Int. Cl.
*G06K 9/00* (2006.01)
*G06T 7/00* (2017.01)
(Continued)

(52) U.S. Cl.
CPC .......... *G06T 7/0016* (2013.01); *A61B 3/0025* (2013.01); *A61B 3/102* (2013.01);
(Continued)

(58) Field of Classification Search
CPC ..... A61B 3/0025; A61B 3/102; A61B 3/1225; G06K 2209/05; G06K 9/6269
(Continued)

(56) References Cited

U.S. PATENT DOCUMENTS

| 6,640,124 B2 * | 10/2003 | Elsner ...................... A61B 3/12 351/221 |
| 7,042,219 B2 * | 5/2006 | Biglieri .................. A61B 5/055 324/309 |

(Continued)

FOREIGN PATENT DOCUMENTS

| EP | 2 703 871 A2 | 3/2014 |
| WO | WO 2010/103085 A1 | 9/2010 |
| WO | WO 2012/126070 A1 | 9/2012 |

OTHER PUBLICATIONS

Abramoff et al., "Retinal Imaging and Image Analysis", IEEE Reviews in Biomedical Engineering, IEEE, USA, vol. 3, 2010, pp. 169-208.

(Continued)

*Primary Examiner* — Charlotte M Baker
(74) *Attorney, Agent, or Firm* — Birch, Stewart, Kolasch & Birch, LLP (57) ABSTRACT

In the context of a method for the analysis of image data representing a three-dimensional volume of biological tissue, the image data comprises a first image representing the volume at a first point in time and a second image representing the volume at a second point in time being different from the first point in time. The method comprises the steps of: a) identifying a first subvolume of the volume represented by the first image having a major extension in a predefined direction and a second subvolume of the volume represented by the second image having a major extension in the predefined direction, whereas the first subvolume and the second subvolume represent a same region of the three- (Continued)

dimensional volume; b) creating a distance matrix from image data of a succession of voxels of the first subvolume in the predefined direction and image data of a succession of voxels of the second subvolume in the predefined direction; and c) analyzing the distance matrix to obtain at least one local measure for a probability of growth of a layer of the biological tissue represented by the first and the second subvolume, along the predefined direction.

14 Claims, 3 Drawing Sheets (51) Int. Cl.
| | |
|---|---|
| A61B 3/00 | (2006.01) |
| A61B 3/10 | (2006.01) |
| A61B 3/12 | (2006.01) |
| G06K 9/62 | (2006.01) |
| G06T 3/00 | (2006.01) |
| G06T 11/00 | (2006.01) |
| G06T 7/62 | (2017.01) |

(52) U.S. Cl.
CPC .......... *A61B 3/1225* (2013.01); *G06K 9/6269* (2013.01); *G06T 3/0093* (2013.01); *G06T 7/62* (2017.01); *G06T 11/008* (2013.01); *G06K 2209/05* (2013.01); *G06T 2207/10101* (2013.01); *G06T 2207/20076* (2013.01); *G06T 2207/30041* (2013.01)

(58) Field of Classification Search
USPC ....... 382/131, 215, 218, 294, 241, 242, 243; 324/209; 600/410, 407, 476; 702/19; 351/246
See application file for complete search history.

(56) References Cited

U.S. PATENT DOCUMENTS

| | | | | |
|---|---|---|---|---|
| 7,483,572 | B2* | 1/2009 | Porikli | G06K 9/50 |
| | | | | 358/1.9 |
| 8,332,016 | B2* | 12/2012 | Stetson | G06T 15/08 |
| | | | | 356/478 |
| 2011/0081055 | A1 | 4/2011 | Bell et al. | |
| 2011/0200242 | A1 | 8/2011 | Takama et al. | |
| 2012/0184845 | A1 | 7/2012 | Ishikawa et al. | |
| 2013/0039557 | A1 | 2/2013 | Wei et al. | |
| 2013/0286354 | A1* | 10/2013 | Stetson | A61B 3/102 |
| | | | | 351/246 |

OTHER PUBLICATIONS

Chiu et al. "Automatic segmentation of seven retinal layers in SDOCT images congruent with expert manual segmentation", Optics Express, vol. 18, No. 18, 2010, pp. 19413-19428.

Dufour et al., "Graph-Based Multi-Surface Segmentation of OCT Data Using Trained Hard and Soft Constraints", IEEE Transactions on Medical Imaging, vol. 32, No. 3, 2013, pp. 531-543.

Kim et al. "Spatial intensity prior correction for tissue segmentation in the developing human brain", 8th IEEE International Symposium on Biomedical Imaging: From Nano to Macro, 20110330 IEEE, 2011, pp. 2049-2052.

* cited by examiner

METHOD FOR THE ANALYSIS OF IMAGE DATA REPRESENTING A THREE-DIMENSIONAL VOLUME OF BIOLOGICAL TISSUE

TECHNICAL FIELD

The invention relates to a method for the analysis of image data representing a three-dimensional volume of biological tissue, the image data comprising a first image representing the volume at a first point in time and a second image representing the volume at a second point in time being different from the first point in time. The invention further relates to a computer program for the analysis of image data representing a three-dimensional volume of biological tissue.

BACKGROUND ART

Age-related Macular Degeneration (AMD) and especially neovascular AMD (nAMD) is the leading cause of blindness in the developed countries in people ageing over 50 years. An increase in vascular permeability leads to abnormal fluid collection within or below the retina that causes visual dysfunction when it involves the center of the macula. This leads to rapidly deteriorating acuity, scarring of the pigment epithelium, and permanent visual loss or blindness.

However, intravitreal injection of antiangiogenic agents, including Ranibizumab (trade name Lucentis®, Novartis, Basel, Switzerland), has been shown to significantly improve the course of nAMD. To reduce the burden of intravitreal injections and to optimize the risk/benefit profile, the progression of nAMD features can be monitored non-invasively by Optical Coherence Tomography (OCT). Prominent nAMD features involve the increase of the thickness of retinal structures. Such an increase may be identified when visually comparing two OCT images of the same region of the retina taken at different times, the temporal distance being several days to several months.

For instance, patients treated with Ranibizumab usually undergo an OCT examination every month. If a significant growth in nAMD features is observed, then a treatment decision is indicated: the patient receives a Ranibizumab injection that day, one month later and two months later (treatment phase). Retreatment can be indicated one month later if the nAMD features have not completely receded. Otherwise, the patient does not receive an injection that day, but regularly indicated maintenance injections (maintenance phase).

The OCT acquisition and the subsequent analysis of OCT acquisitions are usually done by skilled personnel, including ophthalmologists. This means that the monitored patients are required to visit a medical practice or specialized unit of a hospital each time an OCT is to be acquired. This puts a considerable burden upon the patients. Furthermore, the frequency of the OCT acquisitions (such as 1 month) is already sort of a compromise between on one hand close monitoring of the development of nAMD and on the other hand the costs and the burden on the patient.

In principle, automatic analysis of OCT acquisitions may alleviate these problems. In recent years, many algorithms have been designed to automatically analyze OCT acquisitions of the retina, cf. Abràmoff M D, Garvin M., Sonka M., *Retinal Imaging and Image Analysis*, IEEE Rev Biomed Eng. 2010; 3:169-208. Most of these algorithms are focused on the segmentation of anatomical structures of the retina such as retinal layers. However, none of these algorithms has proven to be satisfactory with respect to automatically providing information on morphological changes, in particular of thickness changes of layers, of the imaged biological tissue, especially if the analysis is to be based on sparse OCT information as may be obtained by non-expensive small OCT devices. Accordingly, an automated method that provides information that is useful for deciding on further treatment of nAMD is still missing.

SUMMARY OF THE INVENTION

It is the object of the invention to create a method for the analysis of image data pertaining to the technical field initially mentioned, that allows for reliably providing information on morphological changes in the imaged biological tissue, in particular if the image data is sparse.

The solution of the invention is specified by the features of claim 1. According to the invention the method comprises the steps of:
a) identifying a first subvolume of the volume represented by the first image having a major extension in a predefined direction and a second subvolume of the volume represented by the second image having a major extension in the predefined direction, whereas the first subvolume and the second subvolume represent a same region of the three-dimensional volume;
b) creating a distance matrix from image data of a succession of voxels of the first subvolume in the predefined direction and image data of a succession of voxels of the second subvolume in the predefined direction; and
c) analyzing the distance matrix to obtain at least one local measure for a probability of growth of a layer of the biological tissue represented by the first and the second subvolume, along the predefined direction.

Accordingly, an inventive computer program for the analysis of image data representing a three-dimensional volume of biological tissue, comprises computer program code adapted to perform the aforementioned steps when run on a computer.

It is to be noted that the three-dimensional volume of biological tissue may be represented by a two-dimensional picture (i.e. a two-dimensional grid of pixels), showing just a slice of the tissue. In this case, a "voxel" is effectively a pixel and is considered to represent a three dimensional volume (e.g. a cubic volume) around the respective location of the slice of the tissue. However, the inventive method is particularly well suited for image data constituted by three-dimensional grids of voxels.

In particular, the predefined direction coincides with an axis of the three-dimensional image data. This facilitates the processing of the image data. A typical temporal distance of the first point in time and the second point in time is 12 h-150 d, in particular 5 d-90 d.

It is to be noted that it is not required that the first subvolume and the second subvolume represent exactly the same region of the analyzed biological tissue, but that there is a region covered by both subvolumes. It is that region (or a part thereof) that will be studied in the subsequent steps.

The distance matrix contains the values of a distance measure (or cost function) with respect to the image data for pairs of voxels (one voxel of the first subvolume and one voxel of the second subvolume). In the simplest case, the distance matrix will be 2-dimensional, or it may have a higher dimension as will be shown below. It is to be noted that in general it will not be necessary to establish the full matrix, but voxels of the first subvolume and of the second subvolume that have a very different position with respect to the predefined direction need not be compared to each other as they will not correspond to the same section of the biological tissue even in cases of substantial change between the images compared.

The result of the aforementioned steps is a local measure for a probability of growth of a layer within the biological tissue represented by the first and the second subvolume, this may be a layer that has already existed in the first image or a new layer that has been detected only in the second image. In this context, "local" means that it relates to a certain position on a plane defined substantially by two axes rectangular to each other and rectangular to the predefined direction.

It has shown that this method, based on the distance matrix, is robust and considerably simpler than traditional image recognition techniques that try to identify specific structures of the biological tissue for subsequently determining the size of these structures. Based on the distance matrix, changes in the thickness of layers of the tissue may be automatically and reliably identified.

In particular, the image data is optical coherence tomography (OCT) image data. In the case of OCT scans the first subvolume and the second subvolume each correspond to an A scan (in ultrasound terminology) at a certain position. The predefined direction corresponds to the depth axis, i.e. the axis along which the A scan is taken. In the following, the depth axis is denoted by y, the two axes perpendicular to the y axis, indicating the position of the corresponding A scan, are denoted by x and z, respectively. In particular, the 3-D OCT image data is obtained from spectral-domain OCT.

In principle, the inventive method may be applied to 3-dimensional image data obtained from other techniques such as angiography, computer tomography, magnetic resonance imaging (MRI), etc.

The inventive method is particularly well suited for the study of human or mammalian retina tissue. In particular, the method allows for the automatic study of the growing of individual layers of the retina, notably in the macula region. Correspondingly, the processed data facilitates the detection of nAMD features and provides information that is useful for deciding on further treatment of nAMD. The method therefore may be used as a decision support tool to help clinicians assess the need for intravitreal injections.

The inventive method does not aim at detecting all nAMD features, namely intraretinal cysts, subretinal fluid, diffuse retinal edema, retinal pigment epithelial detachment and subretinal tissue. Instead, it detects local retinal growths in 3-D OCT volumes. This detection is less sensitive to image quality variations than image recognition based approaches and thus more robust.

The invention is not restricted to the study of retina tissue. Other biological tissues may be studied using the inventive method, in particular if thickness changes (increase or decrease) in layers of these tissues over time are of interest. An example is the progression of Alzheimer's disease observed in MRI images.

Preferably, the step of analyzing the distance matrix comprises the substep of obtaining a warping function corresponding to a path linking a predetermined start point with a predetermined end point of the distance matrix, a sum of distances given by the distance matrix being minimal along the path. The shortest distance may be determined by employing a pathfinding algorithm known as such, e.g. the Dijkstra algorithm.

This approach is inspired by the "dynamic time warping" method known from the analysis of temporal sequences, e.g. in speech recognition or areas such as seismology. The warping function corresponds to an optimal match between the voxels of the first subvolume and the voxels of the second subvolume. Generally spoken, each voxel of the first subvolume is paired with one voxel in the second subvolume. If one voxel in the first subvolume is paired with multiple voxels in the second subvolume, it probably means that the tissue recorded in that voxel has grown between the two acquisitions or that fluid has appeared right below or above that voxel.

Correspondingly, changes in thicknesses of individual layers of the biological tissue represented by the image data will lead to characteristic changes of the path represented by the warping function. Analysis of the warping function thus yields information that is useful for obtaining a local measure for a probability of growth of a layer of the biological tissue along the predefined direction.

In the case of studying retina tissue, the start point along the predefined direction will correspond in particular to the inner limiting membrane of the retina, the end point will correspond to the choroid.

Advantageously, the step of analyzing the distance matrix comprises the further substep of comparing the path with a reference path, the local measure for the probability of growth corresponding to the overall difference between the path and the reference path. In particular, the reference path is chosen to correspond to a situation where there is no change between the compared image data of the succession of voxels of the first subvolume and the image data of the succession of voxels of the second subvolume. In the most simple case, using a two-dimensional distance matrix, the reference path is a straight line linking the start point with the end point, i.e. the reference path shows no warping. If the column of the matrix indicates the y position of the reference (first) subvolume and the row of the matrix indicates the y position of the current (second) subvolume, the diagonal runs from the upper left corner (start point) to the lower right corner (end point). A warping function having a path below the reference path (diagonal) indicates that a growth in a tissue layer is detected. Accordingly, the area between the reference path and the path defined by the warping function is a measure for an increase in thickness of layers of the biological tissue.

Different measures for comparing the overall difference between the path and the reference path may be applied. Most preferred is a measure that is proportional to a size of an area delimited by the path and the reference path. In case of a two-dimensional distance matrix, the area is simply the ordinary geometrical area measured in arbitrary units, in case of higher-dimensional distance matrices a measure for the area of a hypersurface will have to be employed. The local measure will be the area determined times a predefined proportionality constant.

Other local measures may include weighting, in particular according to a subset of the distance values of the distance matrix. Furthermore, instead of the area between the path and the reference path other criteria such as the length of the path or the length difference between path and reference path may be employed.

Preferably, a growth map is obtained, constituted by the local measures for the probability of growth depending on a position in a plane perpendicular to the predefined direction. In the case of three-dimensional image data constituted by a (truly) three-dimensional grid of the (x, z) plane the local measure is determined as described above, i.e. for all these points a measure for the probability of growth along the predefined direction is obtained and collected in the two-dimensional growth map. If the image data is two-dimensional, the growth map will be one-dimensional. The growth map is a very helpful basis for the further analysis.

In particular, a global measure for the probability of growth of a layer of the biological tissue represented by the first and the second image, along the predefined direction, is obtained by application of a machine learning algorithm, to the growth map. Using a machine learning algorithm allows for systematically including the knowledge of specialists in the field of analysis of the respective image data. The machine learning algorithm may be directly applied to the growth map, i.e. the local measures stored in the map, or the values of the growth map may be preprocessed, e.g. further consolidated, prior to application of the machine learning algorithm.

In a preferred embodiment, the method includes the step of extracting a global growth feature vector from the growth map and by application of a support vector machine algorithm to the global growth feature vector in order to classify the global growth probability. In contrast to the local measure which provides a probability of growth along essentially a line starting at a given (x, z) coordinate, the global growth feature vector relates to the growth probability within the entire volume of the biological tissue studied. Extracting the global growth feature vector is a preprocessing step for the machine learning algorithm, and the latter will be applied to the global growth feature vector in order to classify the global growth probability, i.e. the global growth feature vector is mapped to the final global growth probability by a Support Vector Classification (SVC) model. Possible classes may be simply "no growth" or "growth" (binary), or intermediate classes may be defined. A decision with respect to further analysis and/or treatment may be taken by the clinician based on the classification.

Preferably, the global growth feature vector comprises at least one average of the local measures and at least one measure of spatial autocorrelation of the local measures. The term "average" is to be understood in a broad sense, as normalization is not strictly measures or of the squares of the local measures or similar. Suitable measures of spatial autocorrelation are e.g. Moran's I or Geary's C. The latter can differentiate dispersed or random local growths (that are likely due to noise) from clustered local growths that are typically observed when nAMD features appear or grow.

It has turned out that the combination of averages as well as of measures of spatial autocorrelation allows for a reliable classification of the global growth probability by machine learning algorithms. In a preferred embodiment, the global growth feature vector is constituted by the following four quantities:

a) the sum of local growth scores;
b) the sum of the squares of local growth scores;
c) Moran's I; and
d) Geary's C.

The global growth feature vector may include other or additional quantities as long as they are chosen to provide information on the probability of growth of a layer of the biological tissue studied.

In a preferred embodiment, the first subvolume has an extension in at least one direction perpendicular to the predefined direction that is larger than an extension in the at least one direction of the second subvolume. Correspondingly, the distance matrix is at least three-dimensional, including a first dimension relating to a position along the predefined direction in the second subvolume and at least two further dimensions relating to a position along the predefined direction and the at least one direction perpendicular to the predefined direction in the first subvolume.

More preferably, the distance matrix is four dimensional, including the first dimension relating to the position along the predefined direction in the second subvolume and three further dimensions relating to a position along the predefined direction and two directions perpendicular to the predefined direction in the first subvolume.

If a warping function is determined, the corresponding path will have at least one additional degree of freedom. Using this 3-D extended version of the Dynamic Time Warping inspired algorithm allows for compensating small offsets or tilts between the compared images, e.g. caused by certain tracking inaccuracies or slight distortions due to a change of orientation of the biological tissue with respect to the imaging device. In ultrasound terminology, the target A-scan (second subvolume) at location (x,z) is not simply matched to the A-scan at location (x,z) in the reference image (first subvolume), but rather to a number of neighbouring A-scans, e.g. those belonging to a thin cylindrical volume centered on the first mentioned (x,z) A-scan.

This means that the two volumes still need to be approximately registered. For instance, in the case of OCT images of the retina taken in different sessions this is achievable with today's equipment. As an example, employing the Heidelberg SLO-based tracking device, two volumes are achieved that are sufficiently registered in a direction perpendicular to the optical axis of the eye. The small residual registration errors will be taken account of by the 3-D extension of the warping algorithm.

Using this technology, the two volumes are not necessarily registered in depth, i.e. along the y-axis. Registration in this direction may be achieved by segmenting the Inner Limiting Membrane (ILM) in both volumes, e.g. by using a graph-cut based algorithm. Then, all A-scans are shifted along the y-axis in order to set the ILM to the y=0 coordinate.

In the most simple case, the first and the second volume will extend only in the predefined direction, i.e. they will correspond to a succession of single voxels. This requires a certain accuracy with respect to the registration of the two images. Furthermore, in order to avoid deterioration of the results due to small residual registration errors the resolution in x and z direction should be fine enough in order to avoid abrupt changes of the layer geometry between neighbouring (x, z) positions.

Advantageously, an intensity of the image data relating to the first subvolume and to the second subvolume is normalized prior to creating the distance matrix. This is especially important if the intensity (luminance value) of the voxels constituting the image data is used for creating the distance matrix. Normalization ensures that the two image sections compared with each other by the inventive method are on a common footing, unaffected by illumination and noise variations between acquisitions. Depending on the imaging technology and the biological tissue analyzed, normalization may be applied once to the entire images or individually to the image data of each subvolume employed to create a distance matrix. A suitable normalization method is application of a median filter.

Normalization may be unnecessary if a quantity is employed to create the distance matrix which is not sensitive to a constant shift of image intensity or if the provided image data has already been normalized in the framework of image acquisition and preprocessing.

In a preferred embodiment, the distance matrix is created based on local gradients of the intensity of the image data of the succession of voxels of the first subvolume in the predefined direction and of the image data of the succession of voxels of the second subvolume, i.e. the distance measure used for building up the distance matrix is based on the difference of these local gradients. Gradient filtering, preferably after normalization as mentioned before, enhances the borders of the features of the biological tissue studied, e.g. of the main retinal features (interface between retinal layers, borders of the nAMD features, etc.). Accordingly, the local gradients constitute a basis for creating a robust distance matrix, largely unaffected by influences that affect the images on a global scale. A possible measure is the absolute difference of the local intensity gradient along the y-axis.

Alternatively, the distance measure is based on other quantities, in particular the intensities itself, preferably after normalization. A possible measure is the absolute difference of the normalized intensities. In principle, it is also possible to combine two or more different distance measures by combining the corresponding distance matrices through a weighted sum.

Other advantageous embodiments and combinations of features come out from the detailed description below and the totality of the claims.

BRIEF DESCRIPTION OF THE DRAWINGS

The drawings used to explain the embodiments show.

In the figures, the same components are given the same reference symbols.

PREFERRED EMBODIMENTS

Figure 1:
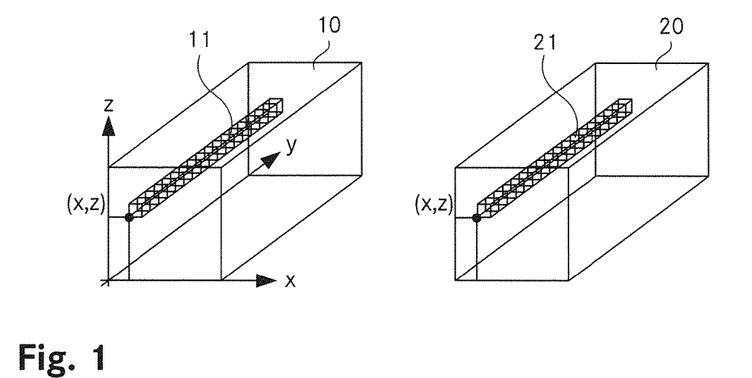
FIG. 1 a schematic representation of a volume of biological tissue represented by image data at two different points in time, including a subvolume to be analysed by an inventive method.

The FIG. 1 is a schematic representation of a volume of biological tissue represented by image data at two different points in time, including a subvolume to be analysed by an inventive method. In the following, the method will be described with reference to 3-D OCT images obtained by spectral domain OCT, taken from the macula region of the human retina. However, the basic steps of the method may be applied to other 3-dimensional images of biological tissue alike. A flow chart of the method according to the invention is given in FIG. 5.

First of all, two images 10, 20 representing essentially the same volume of the given tissue, taken at different points in time, e.g. with a temporal distance of 30 days, are obtained (step 101). The images are composed of a number of voxels that are arranged in a regular grid, the directions along the grid being denoted by x, y, and z, respectively. The two images 10, 20 are approximately registered in a direction perpendicular to the optical axis of the eye, i.e. in the x-z plane, this may be achieved with today's OCT acquisition devices, e.g. by those featuring fundus SLO tracking (developed by Heidelberg Engineering). The y-axis is the depth axis and runs parallel to the optical axis of the eye.

In the given example, both volumes are constituted by 49×49×496 voxels, i.e. comparably sparse. It is to be noted, that the two volumes are not necessarily registered in depth, i.e. along the y-axis. Therefore, the Inner Limiting Membrane (ILM) is segmented in both volumes, using a graph-cut based algorithm, described in Dufour P A, Ceklic L, Abdillahi H et al., *Graph-based multi-surface segmentation of OCT data using trained hard and soft constraints*, IEEE Trans Med Imaging. 2013; 32:531-43. Other known algorithms are applicable. Then, all A-scans are shifted along the y-axis in order to set the ILM to the y=0 coordinate.

Figure 5:
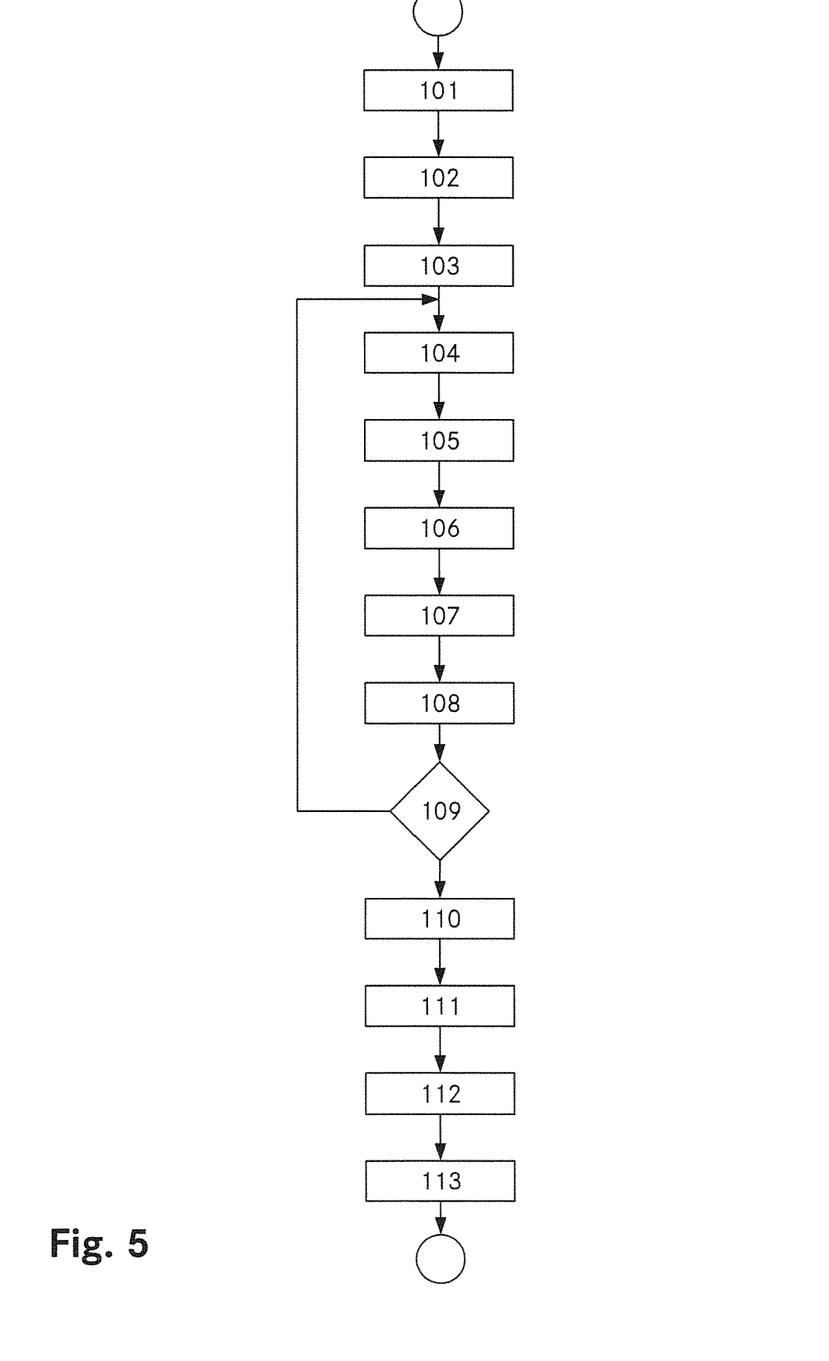
FIG. 5 a flow diagram of a method according to the invention.

When aligning two A-scans from consecutive acquisitions, direct comparison of voxel intensities is not reliable due to illumination and noise variations between acquisitions. As a first preprocessing step 102, a median filter of unit radius is thus applied to remove the noise. As a second preprocessing step 103, a gradient filter is applied to enhance the borders of the main retinal features (interface between retinal layers, borders of the nAMD features, etc.).

The 3-D images are compared A-scan per A-scan, i.e. the A-scan 11 at coordinate (x, z) in the volume represented by the first image 10 is obtained (step 104) and the A-scan 21 at coordinate (x, z) in the volume represented by the second image 20 is obtained (step 105). Both A-scans 11, 21 are subvolumes of the volumes represented by the images 10, 20 and consist of a linear succession of voxels having coordinates (x, y, z), where x and z are constant (and identical for the subvolumes compared to each other) and where the main extension of the A-scans 11, 21, i.e. of the subvolumes, is in the y-direction. The A-scans 11, 21 are then compared to each other.

Figure 2:
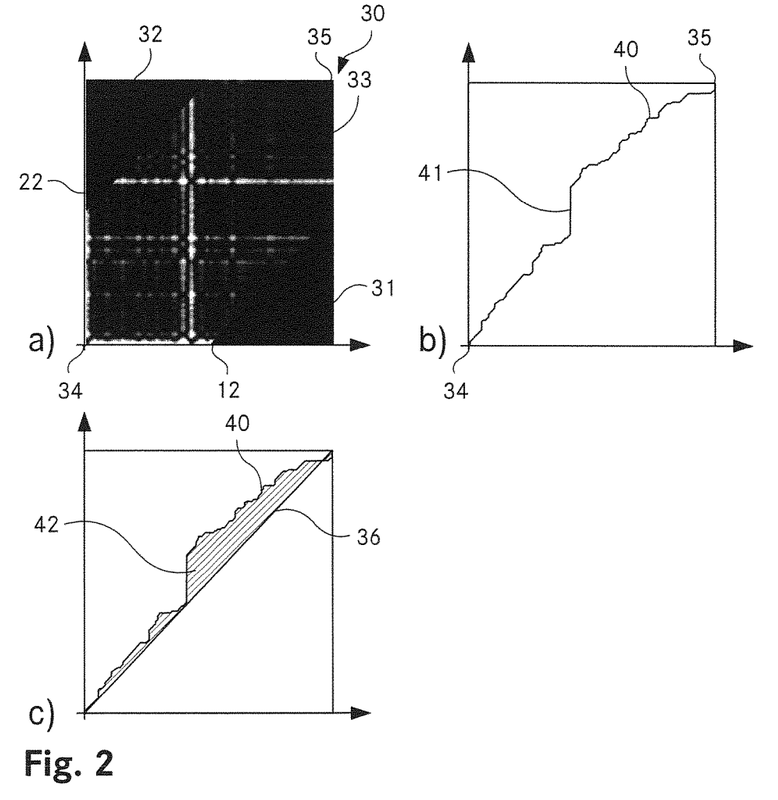
FIG. 2 a) voxel-wise distances with respect to the intensity gradient; b) the shortest distance path corresponding to the voxel-wise distances; c) the area between the shortest distance path and a reference path.

Based on the filtered images, for each pair of A-scans at a respective (x, z) coordinate the voxel-wise distance with respect to the intensity gradient is determined (step 106), i.e. each voxel in the reference A-scan 11 is compared to each voxel in the target A-scan 21, unless their y-coordinates are too distant. The resulting distance matrix 30 is shown in FIG. 2a), where the axes run along the y-coordinate for the reference A-scan 11 ($y_1$ axis 12) and along the y-coordinate for the target A-scan 21 ($y_2$ axis 22): The black triangular areas 31, 32 at the matrix corners are due to the exclusion of areas where |y1−y2| exceeds a certain threshold. The bright lines 33 in the distance matrix 30 correspond to the enhanced borders of retinal features.

Next, a sequence alignment strategy similar to Dynamic Time Warping (DTW) in signal processing is applied to the two A-scans 11, 21 to be compared. Based on the voxel-wise distance matrix 30, the minimal distortion path 40 between the two A-scans 11, 21, from the ILM 34 (bottom left corner) to the choroid 35 (top right corner) is found, using the well-known Dijkstra algorithm in the graph associated with the voxel-wise distance matrix 30 (step 107). The resulting path 40 is shown in FIG. 2b) in the same coordinates as FIG. 2a). It is the path leading from the ILM 34 to the choroid 35 where the sum of voxel-wise distance values given by the distance matrix 30 along the path is minimal.

If one voxel in the first A-scan is paired with multiple voxels in the second A-scans, it probably means that the tissue recorded in that voxel has grown between the two acquisitions or that fluid has appeared right below or above that voxel. As can be seen from FIG. 2b), this situation is given in region 41 of the path 40. It is to be noted that the use of the gradient filter enforces the main retinal layers to be aligned in the minimal distortion path 40.

A path running along the diagonal 36 of the distance matrix 30 corresponds to the situation of identical images (no change). A minimal distortion path 40 going above the diagonal 36 indicates that a retinal growth is detected. Therefore, the area 42 above the diagonal 36 and below the minimal distortion path 40 is used as a local retinal growth score, see FIG. 2c), which again employs the same coordinates as FIGS. 2a) and 2b) (step 108).

The aforementioned steps are repeated as long as not all (x, z) coordinates have been analyzed (decision 109).

Figure 3:
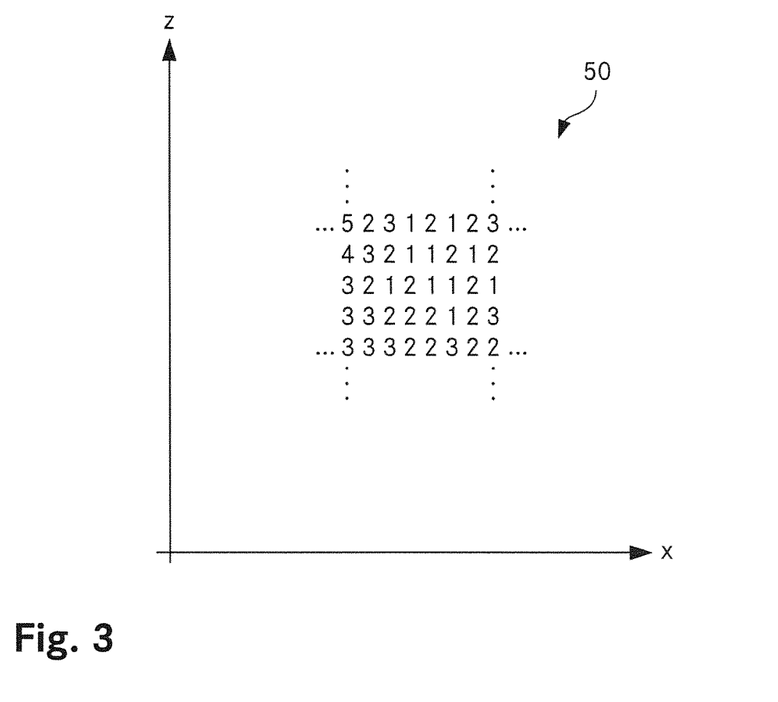
FIG. 3 a schematic representation of a growth map including the local measures for the probability of growth depending on a position on a plane perpendicular to the depth axis.

Next, based on the local retinal growth scores for each (x, z), a growth map 50 is established by repeating the aforementioned steps (step 110). The growth map 50 basically indicates the value of the local retinal growth score s (x, z) as a function of the x- and z-coordinates, i.e. depending on the position in a plane perpendicular to the optical axis of the eye. In FIG. 3, the growth map 50 is schematically represented. It is to be noted that the indicated numbers are merely for illustrative purpose, usually, the score will not be an integer number but just a value indicating the area 42 determined in the previous step.

Next, a global growth probability for the consecutive volumes is calculated (step 111). For that purpose, a global growth feature vector is extracted from the retinal growth map 50. This feature vector is constituted as follows:

$$\begin{pmatrix} \sum_{x,z} s(x, z) \\ \sum_{x,z} s^2(x, z) \\ I \\ C \end{pmatrix}$$

where the first two features simply average the local growth scores s (x, z) (given by the retinal growth map) using either a sum or a sum of squares. The last two features are spatial autocorrelation features, namely Moran's I and Geary's C. The latter two can differentiate dispersed or random local growths (that are likely due to noise) from clustered local growths that are typically observed when nAMD features appear or grow.

Finally, this global growth feature vector is mapped to a global growth probability using a Support Vector Classification (SVC) model (step 112). The SVC also provides an optimal cut-off on the global growth probability. So the algorithm produces binary outputs: 'growth' or 'no growth'. If the output (step 113) is 'growth', a health professional should carry out additional examinations and finally make a treatment decision.

The SVC algorithm has been trained using a training dataset of OCT images, assessed by skilled professional ophthalmologists. A standard training strategy has been adopted for the SVC model: the parameter values (the optimal soft margin parameter C, the optimal kernel function and the optimal kernel function parameters) have been found by two-fold cross-validation. Then the classifier has been retrained in the entire training set using the optimal set of parameters. There have been as many training samples as (x,z) locations in the training set.

Figure 4:
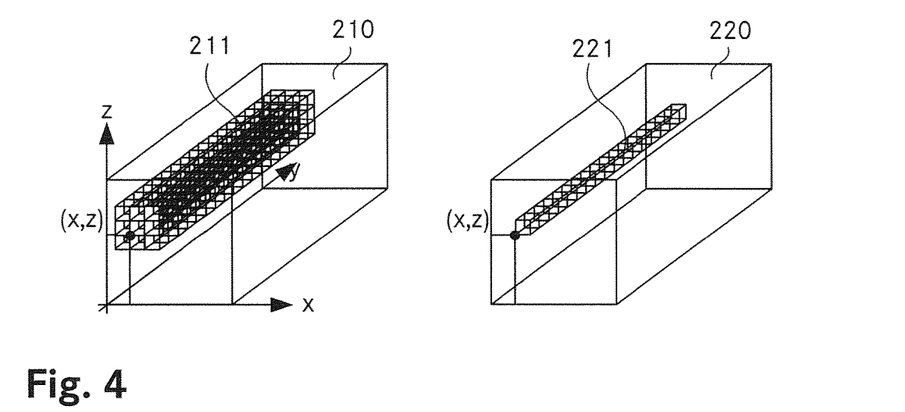
FIG. 4 a schematic representation of a volume of biological tissue represented by image data at two different points in time, including a subvolume to be analysed by a variant of the inventive method.

The FIG. 4 is a schematic representation of a volume of biological tissue represented by image data at two different points in time, including a subvolume to be analysed by a variant of the inventive method.

In order to deal with small (residual) registration errors in the plane perpendicular to the optical axis of the eye, the target A-scan 221 at location (x,z) of the second image 220 is not simply matched to the A-scan at location (x,z) in the earlier OCT image 210, but rather to a thin quasi-cylindrical volume 211 centered on that (x,z) A-scan. The search for the minimal distortion path is similar except that it operates in a four-dimensional voxel-wise matrix (one dimension from the target image 220 and three dimensions from the earlier image 210) rather than a two-dimensional matrix.

The invention is not restricted to the aforementioned method. As described above, some steps of the method may be replaced by alternative algorithms. Furthermore, the method is applicable to other tissues and image data stemming from other imaging techniques.

In summary, it is to be noted that the invention creates a method for the analysis of image data, that allows for reliably providing information on thickness changes in the imaged biological tissue.

The invention claimed is:

1. A method for the analysis of image data representing a three-dimensional volume of biological tissue to obtain a local measure for a probability of growth of a layer of the biological tissue along a predefined direction of an axis of the image data, the image data comprising a first image representing the volume at a first point in time and a second image representing the volume at a second point in time being different from the first point in time, the method comprising the steps of:
   a) identifying a first subvolume of the volume represented by the first image having a major extension in the predefined direction and a second subvolume of the volume represented by the second image having a major extension in the predefined direction, whereas the first subvolume and the second subvolume represent a same region of the three-dimensional volume;
   b) creating a distance matrix from image data of a succession of voxels of the first subvolume in the predefined direction and image data of a succession of voxels of the second subvolume in the predefined direction;
   c) analyzing the distance matrix to obtain at least one local measure for a probability of growth of a layer of the biological tissue represented by the first and the second subvolume, along the predefined direction, for use in determining morphological changes in the biological tissue.

2. The method as recited in claim 1, wherein the step of analyzing the distance matrix comprises the substep of obtaining a warping function corresponding to a path linking a predetermined start point with a predetermined end point of the distance matrix, a sum of distances given by the distance matrix being minimal along the path.

3. The method as recited in claim 2, wherein the step of analyzing the distance matrix comprises the further substep of comparing the path with a reference path, the local measure for the probability of growth corresponding to the overall difference between the path and the reference path.

4. The method as recited in claim 3, wherein the local measure for the probability of growth is proportional to a size of an area delimited by the path and the reference path.

5. The method as recited in claim 1, wherein a growth map is obtained, constituted by the local measures for the probability of growth depending on a position in a plane perpendicular to the predefined direction.

6. The method as recited in claim 5, wherein a global measure for the probability of growth of a layer of the biological tissue represented by the first and the second image, along the predefined direction, is obtained by application of a machine learning algorithm, to the growth map.

7. The method as recited in claim 6, wherein the step of extracting a global growth feature vector from the growth map and by application of a support vector machine algorithm to the global growth feature vector in order to classify the global growth probability.

8. The method as recited in claim 7, wherein the global growth feature vector comprises at least one average of the local measures and at least one measure of spatial autocorrelation of the local measures.

9. The method as recited in claim 1, wherein the first subvolume has an extension in at least one direction perpendicular to the predefined direction that is larger than an extension in the at least one direction of the second subvolume, and in that the distance matrix is at least three-dimensional, including a first dimension relating to a position along the predefined direction in the second subvolume and at least two further dimensions relating to a position along the predefined direction and the at least one direction perpendicular to the predefined direction in the first subvolume.

10. The method as recited in claim 1, wherein prior to creating the distance matrix an intensity of the image data relating to the first subvolume and to the second subvolume is normalized.

11. The method as recited in claim 1, wherein the distance matrix is created based on local gradients of the intensity of the image data of the succession of voxels of the first subvolume in the predefined direction and of the image data of the succession of voxels of the second subvolume.

12. The method as recited in claim 1, wherein the image data is optical coherence tomography image data.

13. The method as recited in claim 1, wherein the biological tissue is human or mammalian retina tissue.

14. A non-transitory computer readable medium having stored thereon a computer program adapted to perform the analysis of image data representing a three-dimensional volume of biological tissue according to the steps of claim 1.

* * * * *